United States Patent [19]

Hubele

[11] Patent Number: 5,393,766
[45] Date of Patent: Feb. 28, 1995

[54] PESTICIDAL COMPOSITIONS

[75] Inventor: Adolf Hubele, Magden, Switzerland

[73] Assignee: Ciba-Geigy Corporation, Ardsley, N.Y.

[21] Appl. No.: 8,030

[22] Filed: Jan. 25, 1993

Related U.S. Application Data

[60] Division of Ser. No. 853,887, Mar. 18, 1992, which is a continuation of Ser. No. 628,772, Dec. 17, 1990.

[30] Foreign Application Priority Data

Dec. 21, 1989 [CH] Switzerland ............... 4580/89
Oct. 26, 1990 [CH] Switzerland ............... 3425/90

[51] Int. Cl.⁶ .................. C07D 417/12; A01N 43/78
[52] U.S. Cl. ...................... 514/365; 548/200
[58] Field of Search ................ 548/200; 514/365

[56] References Cited

U.S. PATENT DOCUMENTS 4,918,089 4/1990 Kusaba ............... 514/365
4,980,363 12/1990 Shimotori ............ 514/365
5,136,042 8/1992 Kuwatsuka .......... 548/188

Primary Examiner—Robert Gerstl
Attorney, Agent, or Firm—Edward McC. Roberts

[57] ABSTRACT

Thiazolyl-5-carbonamide derivatives of formula I

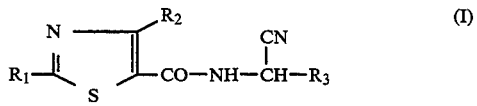

wherein $R_3$ is furanyl or thienyl and $R_1$ and $R_2$ are as defined herein, have valuable microbicidal activity. They can be used in the form of compositions for controlling or preventing plant diseases.

13 Claims, No Drawings

PESTICIDAL COMPOSITIONS

This is a division of Ser. No. 853,887, filed Mar. 18, 1992, which is a continuation of Ser. No. 628,772, filed Dec. 17, 1990, now abandoned.

The present invention relates to novel thiazolyl-5-carbonamide derivatives of formula I below. The invention relates also to the preparation of those compounds and to agrochemical compositions that contain at least one of those compounds as active ingredient. The invention relates also to the preparation of the said compositions and to the use of the compounds or the compositions for controlling microorganisms, especially plant-destructive microorganisms, particularly fungi.

The compounds according to the invention correspond to the general formula I and include the acid addition salts and metal salt complexes thereof.

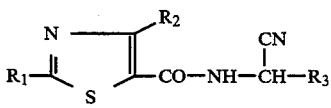

In this formula:

$R_3$ is 2-furanyl, 2-thienyl, 3-furanyl or 3-thienyl;

$R_1$ and $R_2$ are each independently of the other a) $C_3-C_6$cycloalkyl that is unsubstituted or substituted by methyl or methylthio, b) the group —$CH_2$—X—$R_4$, and c) one of the two substituents $R_1$ and $R_2$ may also be hydrogen or $C_1-C_4$alkyl, wherein X is oxygen or sulfur, and $R_4$ is $C_1-C_4$alkyl that may be unsubstituted or substituted by halogen or, in the case of $C_2-C_4$alkyl, also by $C_1-C_3$alkoxy, or wherein $R_4$ is $C_3-C_4$alkenyl, $C_3-C_4$alkynyl or a phenyl group or benzyl group of which the aromatic ring is unsubstituted or may be substituted by halogen, $C_1-C_2$alkyl, $C_1-C_2$alkoxy, $CF_3$ or by $NO_2$.

Depending upon the number of carbon atoms indicated, alkyl by itself or as a constituent of another substituent, such as haloalkyl or alkoxy, is to be understood as being, for example, methyl, ethyl, propyl, butyl, and the isomers isopropyl, isobutyl, tert.-butyl or sec.-butyl. Halogen, also referred to as Hal, is fluorine, chlorine, bromine or iodine. Haloalkyl indicates mono- to perhalogenated radicals, for example $CHCl_2$, $CH_2F$, $CCl_3$, $CH_2Cl$, $CHF_2$, $CF_3$, $CH_2CH_2Br$, $C_2Cl_5$, $CH_2Br$, $CHBrCl$ etc. Depending upon the number of carbon atoms indicated, cycloalkyl is, for example, cyclopropyl, cyclobutyl, cyclopentyl or cyclohexyl.

The compounds of formula I are oils or solids that are stable at room temperature and are distinguished by valuable microbicidal properties. They can be used preventively and curatively in the agricultural sector or related fields for controlling plant-destructive microorganisms. The compounds of formula I according to the invention are, when used in low concentrations, distinguished not only by excellent microbicidal, especially fungicidal, activity but also by especially good plant tolerability.

The compounds of formula I have an asymmetric carbon atom adjacent to the nitrile group. They can therefore be cleaved into optical antipodes in customary manner. These antipodes have different microbicidal actions.

The invention relates both to the free compounds of formula I and to the addition salts thereof with inorganic and organic acids and the complexes thereof with metal salts.

Salts according to the invention are especially addition salts with acceptable inorganic or organic acids, for example hydrohalic acids, for example hydrochloric, hydrobromic or hydriodic acid, sulfuric acid, phosphoric acid, phosphorous acid, nitric acid, or organic acids such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid or 1,2-naphthalenedisulfonic acid.

Metal salt complexes of formula I consist of the underlying organic molecule and an inorganic or organic metal salt, for example the halides, nitrates, sulfates, phosphates, acetates, trifluoroacetates, trichloroacetates, propionates, tartrates, sulfonates, salicylates, benzoates etc. of the elements of main group II, such as calcium and magnesium, and main groups III and IV, such as aluminium, tin or lead, and of subgroups I to VIII, such as chromium, manganese, iron, cobalt, nickel, copper, zinc, etc. Subgroup elements of the 4th period are preferred. The metals can be present in any of the various valencies attributed to them. The metal complexes may be mono- or poly-nuclear, that is to say they may contain one or more organic molecule components as ligands.

An important group of phytofungicides and insecticides comprises those of formula I wherein one of the two substituents $R_1$ and $R_2$ is $C_3-C_6$cycloalkyl that is unsubstituted or substituted by methyl or methylthio, and the other substituent is d) cyclobutyl, cyclopropyl, methylcyclopropyl or methylthiocyclopropyl, e) the group —$CH_2$—X—$R_4$ or f) hydrogen or $C_1-C_4$alkyl, while $R_3$, X and $R_4$ are as defined above.

Here and hereinbelow this group is referred to as compound group IA.

Among the compounds of group IA, special mention should be made of those wherein one of the two substituents $R_1$ and $R_2$ is $C_3-C_6$cycloalkyl and the other is cyclobutyl or cyclopropyl, while $R_3$ is as defined above (group 1AA), and of those, in turn, those compounds wherein $R_1$ and $R_2$ are cyclopropyl.

Important compounds are also those of group IA wherein $R_1$ is $C_3-C_6$cycloalkyl that is unsubstituted or substituted by methyl or methylthio, $R_2$ is hydrogen, $C_1-C_4$alkyl or the group —$CH_2$—X—$R_4$, X is oxygen or sulfur, and $R_4$ is $C_1-C_4$alkyl that is unsubstituted or substituted by fluorine or, in the case of $C_2-C_4$alkyl, may also be substituted by $C_1-C_3$alkoxy; or wherein $R_4$ is allyl, propargyl, phenyl or benzyl, the aromatic rings of the latter radicals being unsubstituted or substituted by one or two of the substituents fluorine, chlorine, methyl, ethyl, methoxy and $CF_3$, while $R_3$ is as defined above (group IB).

Those compounds of group IB wherein X is oxygen are preferred (group IBB).

Important compounds within group IBB are those wherein $R_1$ is cyclobutyl, cyclopropyl, methylcyclopropyl or methylthiocyclopropyl, $R_2$ is hydrogen, $C_1$-$C_4$alkyl or —$CH_2$—O—$R_4$, wherein $R_4$ is $C_1$-$C_4$alkyl that is unsubstituted or substituted by fluorine, methoxy or by ethoxy, or wherein $R_4$ is allyl, propargyl, phenyl, chlorophenyl, fluorophenyl, benzyl, chlorobenzyl or fluorobenzyl (=subgroup Ib).

Preferred compounds within group Ib are those wherein $R_1$ is cyclopropyl, $R_2$ is hydrogen, $C_1$-$C_4$alkyl or —$CH_2$—O—$R_4$, wherein $R_4$ is methyl, ethyl, fluoromethyl, difluoromethyl, trifluoroethyl, allyl, propargyl, phenyl or benzyl, while $R_3$ is as defined above (=subgroup Ibb).

Especially preferred compounds within group Ibb are those wherein $R_2$ is hydrogen, $C_1$-$C_3$alkyl, methoxymethyl or ethoxymethyl.

Important compounds are also those of group Ia wherein $R_1$ is hydrogen, $C_1$-$C_4$alkyl or the group —$CH_2$—X—$R_4$, X is oxygen or sulfur, and $R_4$ is $C_1$-$C_4$alkyl that is unsubstituted or substituted by fluorine or, in the case of $C_2$-$C_4$alkyl, may also be substituted by $C_1$-$C_3$alkoxy; or wherein $R_4$ is allyl, propargyl, phenyl or benzyl, the aromatic tings of the latter radicals being unsubstituted or substituted by one or two of the substituents fluorine, chlorine, methyl, ethyl, methoxy and $CF_3$, while $R_2$ is $C_3$-$C_6$cycloalkyl that is unsubstituted or substituted by methyl or methylthio, while $R_3$ is as defined above (=group IC), especially those wherein X is oxygen (=group ICC).

Within that group ICC, preferred compounds are those wherein $R_1$ is hydrogen, $C_1$-$C_4$alkyl or —$CH_2$—O—$R_4$, $R_2$ is cyclobutyl, cyclopropyl, methylcyclopropyl or methylthiocyclopropyl, and $R_4$ is $C_1$-$C_4$alkyl that is unsubstituted or fluoro-substituted or, in the case of $C_2$-$C_4$alkyl, may also be substituted by methoxy or ethoxy; or wherein $R_4$ is allyl, propargyl, phenyl, chlorophenyl, fluorophenyl, benzyl, chlorobenzyl or fluorobenzyl, while $R_3$ is as defined above (=subgroup Ic).

Especially preferred compounds within subgroup Ic are those wherein $R_2$ is cyclopropyl, and $R_4$ is methyl, ethyl, fluoromethyl, difluoromethyl, trifluoroethyl, allyl, propargyl, phenyl or benzyl (=subgroup Icc).

Of those compounds, special mention should be made of those wherein $R_1$ is hydrogen, $C_1$-$C_3$alkyl, methoxymethyl or ethoxymethyl.

Important compounds are also those thiazolyl-5-carbonamide derivatives of formula I wherein one of the two substituents $R_1$ and $R_2$ is the group —$CH_2$—X—$R_4$ and the other substituent is hydrogen, $C_1$-$C_4$alkyl or —$CH_2$—X—$R_4$, X is oxygen or sulfur, $R_3$ is as defined above, and $R_4$ is $C_1$-$C_4$alkyl that is unsubstituted or substituted by fluorine or, in the case of $C_2$-$C_4$alkyl, may also be substituted by $C_1$-$C_3$alkoxy; or wherein $R_4$ is allyl, propargyl, phenyl or benzyl, the aromatic rings of the latter radicals being unsubstituted or substituted by one or two of the substituents fluorine, chlorine, methyl, ethyl, methoxy and $CF_3$ (=subgroup ID).

Of the compounds of group ID, special mention should be made of those wherein $R_1$ is the group —$CH_2$—O—$R_4$, $R_2$ is hydrogen, $C_1$-$C_4$alkyl or —$CH_2$—O—$R_4$, $R_3$ is as defined above, and $R_4$ is $C_1$-$C_4$alkyl that is unsubstituted or substituted by fluorine, methoxy or by ethoxy, or wherein $R_4$ is allyl, propargyl, phenyl, chlorophenyl, fluorophenyl, benzyl, chlorobenzyl or fluorobenzyl (subgroup IDD).

Preferred compounds of formula I in subgroup IDD are those wherein $R_4$ is methyl, ethyl, fluoromethyl, difluoromethyl, trifluoroethyl, allyl, propargyl, phenyl or benzyl (=subgroup Id).

Especially preferred compounds in the last-mentioned subgroup Id are those wherein $R_2$ is hydrogen or $C_1$-$C_3$alkyl.

Especially preferred compounds in subgroup Id are also compounds wherein $R_1$ and $R_2$ are each independently of the other methoxymethyl or ethoxymethyl.

Among the compounds of group ID, special mention should be made of those compounds wherein $R_1$ is hydrogen, $C_1$-$C_4$alkyl or the group —$CH_2$—O—$R_4$, $R_2$ is —$CH_2$—O—$R_4$, $R_3$ is as defined above and $R_4$ is $C_1$-$C_4$alkyl that is unsubstituted or substituted by fluorine, methoxy or by ethoxy, or wherein $R_4$ is allyl, propargyl, phenyl, chlorophenyl, fluorophenyl, benzyl, chlorobenzyl or fluorobenzyl (=subgroup IE).

Preferred compounds of group IE are those wherein $R_4$ is methyl, ethyl, fluoromethyl, difluoromethyl, trifluoroethyl, allyl, propargyl, phenyl or benzyl (=subgroup IEE).

Especially preferred compounds of group IEE are those wherein $R_1$ is hydrogen or $C_1$-$C_3$alkyl.

Furthermore, an important group of phytofungicides comprises those compounds of formula I wherein either a) $R_1$ is $CH_3$, $C_2H_5$, n—$C_3H_7$, iso$C_3H_7$, $CH_2$—O—$CH_3$, $CH_2$—O—$C_2H_5$ or $CH_2$—O—$CHF_2$ or cyclopropyl, and $R_2$ is cyclopropyl, or wherein b) $R_1$ is $CH_2$—O—$CH_3$, $CH_2$—O—$C_2H_5$, $CH_2$—O—$CHF_2$ or cyclopropyl, and $R_2$ is $C_1$-$C_3$alkyl, and $R_3$ is as defined above (subgroup Alpha).

Among the compounds of the group Alpha, mention should be made of a preferred subgroup wherein $R_1$ is $CH_3$, $C_2H_5$, n—$C_3H_7$ or iso—$C_3H_7$, and $R_2$ is cyclopropyl (subgroup Beta).

Furthermore, among the compounds of the group Alpha, mention should be made of a further preferred subgroup wherein $R_1$=$CH_2$—O—$CH_3$, $CH_2$—O—$C_2H_5$ or cyclopropyl and $R_2$=$CH_3$, $C_2H_5$, n—$C_3H_7$, iso-$C_3H_7$ or cyclopropyl (subgroup Gamma).

Compounds of formula I are obtained by reaction of the thiazolyl-5-carboxylic acid of formula V

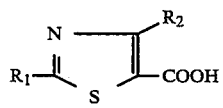

or an acid halide, an ester or an acid anhydride thereof, with an aminoacetonitrile of formula II

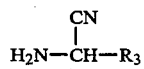

in the presence or absence of a condensation agent or an acid acceptor, the substituents $R_1$, $R_2$ and $R_3$ being as defined under formula I.

It is advantageous to use the amine component II in slight excess with respect to component V (for example up to 2 molar equivalents).

An acid halide is to be understood as being especially a chloride, bromide or iodide, and acid esters are to be understood as being the readily reactive derivatives of $C_1$–$C_6$ alcohols, for example inter alia methyl, ethyl, propyl, isopropyl, butyl, tert.-butyl and amyl esters. The reaction of V with II is effected in the absence or preferably in the presence of a condensation agent or an acid acceptor (proton acceptor).

An acid halide of formula V can also be obtained in situ from the thiazolyl-5-carboxylic acid by reaction thereof with reactant II in the presence of a thionyl halide, for example $SOCl_2$, and imidazole. This process variant is included in the above-mentioned process.

The temperature range for the reaction is from $-20°$ C. to $150°$ C., preferably from $-5°$ C. to $80°$ C.

The proton acceptors used may be, for example, inorganic or organic bases, for example alkali metal or alkaline earth metal compounds, for example the hydroxides, oxides or carbonates of lithium, sodium, potassium, magnesium, calcium, strontium and barium, or alternatively hydrides, for example sodium hydride. Organic bases that may be mentioned are, for example, tertiary amines, such as triethylamine, triethylenediamine, pyridine and 4-dimethylaminopyridine.

Although not absolutely necessary, solvents or diluents may advantageously be used for the reaction. Examples that may be mentioned are: halogenated hydrocarbons, especially chlorinated hydrocarbons, such as tetrachloroethylene, tetrachloroethane, dichloropropane, methylene chloride, dichlorobutane, chloroform, carbon tetrachloride, trichloroethane, trichloroethylene, pentachloroethane, 1,2-dichloroethane, 1,1-dichloroethane, 1,2-cis-dichloroethylene, chlorobenzene, fluorobenzene, bromobenzene, dichlorobenzene, dibromobenzene, chlorotoluene, trichlorotoluene; ethers, such as ethyl propyl ether, methyl tert.-butyl ether, n-butyl ethyl ether, di-n-butyl ether, diisobutyl ether, diisoamyl ether, diisopropyl ether, anisole, cyclohexyl methyl ether, diethyl ether, ethylene glycol dimethyl ether, tetrahydrofuran, dioxane, thioanisole, dichlorodiethyl ether, nitrohydrocarbons, such as nitromethane, nitroethane, nitrobenzene, chloronitrobenzene, o-nitrotoluene; nitriles such as acetonitrile, butyronitrile, isobutyronitrile, benzonitrile, m-chlorobenzonitrile; aliphatic or cycloaliphatic hydrocarbons, such as heptane, hexane, octane, nonane, cymene, petroleum fractions within a boiling point range of from $70°$ C. to $190°$ C., cyclohexane, methylcyclohexane, decalin, petroleum ether, ligroin, trimethylpentane, such as 2,3,3-trimethylpentane; esters, such as ethyl acetate, acetoacetic acid esters, isobutyl acetate; amides, for example formamide, methylformamide, dimethylformamide; ketones, such as acetone, methyl ethyl ketone; optionally also water. Mixtures of said solvents and diluents also come into consideration.

The starting materials of formula II can be obtained in accordance with the Strecker synthesis by reaction of the aldehyde III with hydrocyanic acid or an alkali cyanide (for example NaCN) in the presence of ammonia or an ammonium salt:

It is advantageous to use a binary solvent system consisting of, on the one hand, an ether (diethyl ether, dioxane, THF etc.) or an aromatic hydrocarbon (benzene, toluene, xylene) and, on the other hand, water and the operation is performed at from $0°$ to $100°$ C.

The starting materials of formula V are obtained by reaction of a thioamide of formula VI with an α-halo-β-keto ester of formula VII to form the thiazolyl-5-carboxylic acid ester Va:

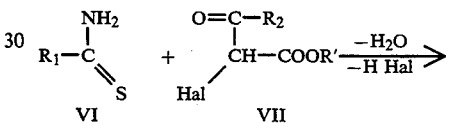

wherein R' is a $C_1$–$C_6$ hydrocarbon, and then, if desired, conversion into the carboxylic acid V by hydrolysis. The reaction can be carried out in a protic solvent, such as an alcohol, or in an aprotic solvent, such as benzene, toluene, cyclohexane etc. In some cases it is advisable to add a proton acceptor, such as sodium acetate/acetic acid or a tertiary base (for example pyridine, triethylamine etc.). The reaction is initially carried out at temperatures of $-60°$ C. to $+40°$ C. preferably $-20°$ C. to $+20°$ C. The temperature is then increased to $+30°$ C. to $+140°$ C., preferably to $+50°$ C. to $+110°$ C. If, for example, the operation is carried out in benzene, toluene or cyclohexane, the water that forms can be removed using a water separator.

In accordance with another process variant, the intermediate of formula V can also be obtained by first acylating the thioamide of formula VI with an acid halide of formula VIII to form an N-acylthioamide of formula IX:

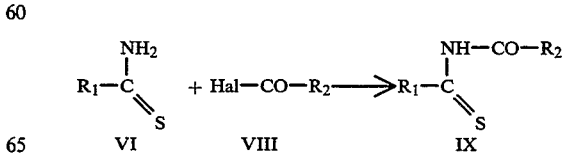

The operation is advantageously carried out in an inch solvent, such as acetonitrile or tetrahydrofuran.

The proton acceptor used is preferably a tertiary base, such as pyridine, triethylamine, 4-dimethylaminopyridine etc.. The reaction should take place in a temperature range of from −40° C. to +80° C., preferably from −20° C. to +20° C. Compound IX is then condensed with a haloester X to form the thiazolyl-5-carboxylic acid ester Va which, if desired, is then convened into V in customary manner:

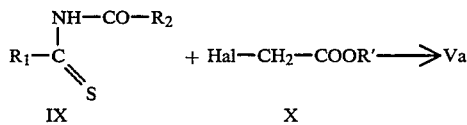

For the cyclisation the N-acylthioamide IX in a protic solvent (for example a lower alcohol) or aprotic solvent is treated with an alcoholate (for example $CH_3$—O—Na) or with NaH at temperatures of from −40° C. to +20° C., preferably from −30° C. to 0° C., and then the halo ester X is added at from −20° C. to +30° C., preferably from −10° C. to +10° C. The reaction mixture is subsequently heated for several hours at from +40° to +120° C., preferably from +60° C. to +100° C., in order to remove the water of reaction.

In the above-mentioned formulae Va to X, $R_1$ and $R_2$ are as defined under formula I.

The present invention relates to the described preparation processes, including all subsidiary steps.

The present invention relates also to the novel intermediates of formula V and their esters with $C_1$–$C_6$alcohols, especially those wherein $R_1$ and $R_2$ are as defined for subgroup Alpha.

Surprisingly, it has now been found that compounds of formula I have, for practical purposes, a very advantageous biocidal spectrum against phytopathogenic microrganisms, especially against fungi. They have very advantageous curative, preventive and, in particular, systemic properties, and can be used for protecting numerous cultivated plants. With the compounds of formula I it is possible to inhibit or destroy the pests which occur in plants or in pans of plants (fruit, blossoms, leaves, stems, tubers, roots) in different crops of useful plants, while at the same time the parts of plants which grow later are also protected, for example, from attack by phytopathogenic microorganisms.

Compounds of formula I are effective, for example, against the phytopathogenic fungi belonging to the following classes: Fungi imperfecti (especially Botrytis, also Pyricularia, Helminthosporium, Fusarium, Septoria, Cercospora and Alternaria); Basidiomycetes (e.g. Rhizoctonia, Hemileia, Puccinia). Furthermore, they are effective against the class of the Ascomycetes (e.g. Venturia and Erysiphe, Podosphaera, Monilinia, Uncinula), but especially against the Oomycetes (e.g. Phytophthora, Peronospora, Bremia, Pythium, Plasmopara). The compounds of formula I can also be used as dressing agents for protecting seeds (fruit, tubers, grains) and plant cuttings against fungus infections and against phytopathogenic fungi which occur in the soil.

The invention relates also to the compositions that contain compounds of formula I as active ingredient, especially plant-protective compositions, and to their use in the agricultural sector or related fields.

The present invention relates also to the preparation of those compositions, which comprises homogeneously mixing the active ingredient with one or more of the compounds or groups of compounds described herein. The invention furthermore relates to a method of treating plants, which comprises applying thereto the novel compounds of formula I or the novel compositions.

Target crops to be protected within the scope of this invention comprise e.g. the following species of plants: cereals (wheat, barley, rye, oats, rice, maize, sorghum and related crops), beet (sugar beet and fodder beet), pomes, drupes and soft fruit (apples, pears, plums, peaches, almonds, cherries, strawberries, gooseberries, raspberries and blackberries), leguminous plants (beans, lentils, peas, soybeans), oil plants (rape, mustard, poppy, olives, sunflowers, coconut, castor oil plants, cocoa, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as tobacco, nuts, coffee, sugar cane, tea, pepper, vines, hops, aubergines, bananas and natural rubber plants, as well as ornamentals.

The compounds of formula I are normally applied in the form of compositions and can be applied to the area or plant to be treated, simultaneously or in succession, with further compounds. These further compounds can be fertilisers, micronutrient donors or other preparations that influence plant growth. They can also be selective herbicides, insecticides, fungicides, bactericides, nematicides, molluscicides or mixtures of several of these preparations, if desired together with further carriers, surfactants or other application-promoting adjuvants customarily employed in the art of formulation.

Suitable carriers and adjuvants can be solid or liquid and correspond to the substances expediently employed in the art of formulation, e.g. natural or regenerated mineral substances, solvents, dispersants, wetting agents, tackifiers, thickeners, binders or fertilisers.

A preferred method of applying a compound of formula I, or an agrochemical composition which contains at least one of said compounds, is foliar application. The number of applications and the rate of application depend on the risk of infestation by the corresponding pathogen. However, the compounds of formula I can also penetrate the plant through the roots via the soil (systemic action) by impregnating the locus of the plant with a liquid composition or by applying the compounds in solid form to the soil, e.g. in granular form (soil application). In paddy rice crops, such granulates can be applied in metered amounts to the flooded rice field. The compounds of formula I may, however, also be applied to seeds (coating) either by impregnating the seeds with a liquid formulation of the active ingredient or by coating them with a solid formulation. In general, any kind of propagation material of a plant may be protected by a compound of formula I, for example the seeds.

The compounds of formula I are used in unmodified form or, preferably, together with the adjuvants conventionally employed in the art of formulation, and are for that purpose advantageously formulated in known manner, e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 25 g to 2 kg a.i./ha, most preferably from 30 g to 300 g a.i./ha.

The formulations, i.e. the compositions, preparations or mixtures containing the compound of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil, or water.

The solid carriers used, e.g. for dusts and dispersible powders, are normally natural mineral fillers such as calcite, talcum, kaolin, montmorillonite or attapulgite.

Especially advantageous application-promoting adjuvants, which can result in a considerable reduction in the application rate, are natural (animal or vegetable) or synthetic phospholipids of the series of the cephalins and lecithins, which can be obtained, for example, from soybeans.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyllaurin salts.

Suitable non-ionic surfactants are polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Representative examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, or benzyl or hydroxy-lower alkyl radicals.

Further surfactants customarily employed in the art of formulation are known to the person skilled in the art or can be taken from the relevant specialist literature.

The anionic, non-ionic or cationic surfactants customarily employed in the art of formulation are known to the person skilled in the art or can be taken from the relevant specialist literature:

"McCutcheon's Detergents & Emulsifiers Annual", Mc Publishing Corp., Glen Rock, N.J., 1988;

M. and J. Ash, "Encyclopedia of Surfactants", Vol. I–III, Chemical Publishing Co., N.Y., 1980–1981;

Dr. Helmut Stache, "Tensid-Taschenbuch", Carl Hanser Verlag, Munich/Vienna, 1981.

The agrochemical compositions usually contain 0.1 to 99%, preferably 0.1 to 95%, of an active ingredient of formula I, 99.9 to 1%, preferably 99.9 to 5%, of a solid or liquid adjuvant, and 0 to 25%, preferably 0.1 to 25%, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers and fertilisers or other active ingredients for obtaining special effects.

The following Examples serve to illustrate the invention but do not limit the scope thereof.

PREPARATION EXAMPLE 1 a) Preparation of 2-methoxymethyl-4-methylthiazole-5-carboxylic acid ethyl ester

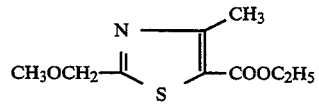

20 g of methoxythioacetamide are added, with vigorous stirring, to 31.3 g of 2-chloroacetoacetic acid ethyl ester in 400 ml of benzene at room temperature and then, using a water separator, heated under reflux for 4½ hours. After cooling to room temperature, the benzenic reaction solution is diluted with 500 ml of ethyl acetate, washed twice using 80 ml of 10% sodium carbonate solution each time and twice using 50 ml of water each time, dried over sodium sulfate and filtered. The solvent mixture is evaporated off. The yellow oil that remains is crystallised by trituration with diisopropyl ether. The beige-coloured crystals melt at 36°–37° C.

b) Preparation of 2-methoxymethyl-4-methylthiazole-5-carboxylic acid $$CH_3OCH_2-\underset{S}{\overset{N}{\underset{\|}{\bigsqcup}}}\overset{CH_3}{\underset{COOH}{}}$$

6.7 g of 85% potassium hydroxide in 1130 ml of ethanol are added at room temperature to 22.1 g of 2-methoxymethyl-4-methylthiazole-5-carboxylic acid ethyl ester and the reaction mixture is then heated under reflux for 18 hours. After cooling, the ethanol is evaporated off and the residue is dissolved in 200 ml of water. After stirring with active carbon, the mixture is filtered over Hyflo and the filtrate is acidified with concentrated hydrochloric acid with vigorous stirring. The resulting yellowish crystals are filtered off, washed with water and dried. After recrystallisation from tetrahydrofuran/petroleum ether (30°-45° C.) (=10:1) the yellowish crystals melt at 168°-169.5° C.

c) Preparation of 2-(2-methoxymethyl-3-methylthiazolyl-5-carbonylamino)-2-(3-thienyl)-acetonitrile

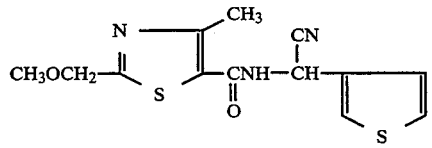

Comp. No. 68

2.38 g of thionyl chloride are added dropwise at 0° C. within a period of ¼ hour, with stirring, to 3.5 g of methoxymethyl-4-methylthiazole-5-carboxylic acid in 40 ml of pyridine. After stirring for one hour at 0° C., 3.5 g of 2-(3-thienyl)-aminoacetonitrile hydrochloride are added and stirring is continued for 18 hours while passing nitrogen through the mixture. After the addition, with stirring, of 200 ml of ice-water and 100 ml of ethyl acetate, the mixture is acidified with 50 ml of concentrated hydrochloric acid; the organic phase is separated off and extraction is carried out again with 70 ml of ethyl acetate. The combined extracts are washed twice using 100 ml of 1N hydrochloric acid each time and once with 100 ml of saturated sodium bicarbonate solution, dried over sodium sulfate and filtered, and the solvent is evaporated off. The yellowish oil that remains is crystallised by trituration with diisopropyl ether. The pale yellow crystals melt at 111°-113° C.

PREPARATION EXAMPLE 2

Preparation of 2-(2-methyl-4-cyclopropylthiazolyl-5-carbonylamino)-2-(3-thienyl)acetonitrile

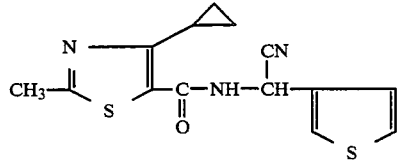

Comp. No. 2

8.75 g of 2-(3-thienyl)-aminoacetonitrile hydrochloride are suspended in 200 ml of ethyl acetate and, after cooling to +5° C., 12 g of triethylamine are added, with stirring, within a period of 5 minutes. With vigorous stirring, 10 g of 2-methyl-4-cyclopropylthiazole-5-carboxylic acid chloride in 100 ml of ethyl acetate are added dropwise at −5° C. within a period of 1 hour and the reaction mixture is then stirred for 2 hours at room temperature; 100 ml of water are added and the aqueous phase is separated off. The ethyl acetate solution is washed twice using 50 ml of water each time, dried over sodium sulfate and filtered, and the solvent is evaporated off. The oil that remains is purified by column chromatography over silica gel (tetrahydrofuran:hexane=1:1). After the eluant mixture has been evaporated off, the initially brown oil is crystallised by trituration with petroleum ether (50°-70° C.) and recrystallised from hexane/dichloromethane. The beige-coloured crystals melt at 108°-110° C.

The following compounds can be prepared in an analogous manner:

TABLE 1

Compounds of formula

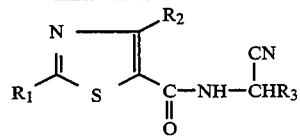

| Comp. No. | $R_1$ | $R_2$ | $R_3$ | Physical constant |
|---|---|---|---|---|
| 1 | H | CP. | $Q_1$ | |
| 2 | —$CH_3$ | CP. | $Q_4$ | m.p. 108–110° C. |
| 3 | —$C_2H_5$ | CP. | $Q_3$ | m.p. 116–117° C. |
| 4 | H | —$CH_2OCH_3$ | $Q_4$ | |
| 5 | CP. | CP. | $Q_4$ | m.p. 93–95° C. |
| 6 | H | CP. | $Q_4$ | |
| 7 | CP. | —$CH_2OCH_3$ | $Q_1$ | |
| 8 | —$CH_3$ | CP. | $Q_1$ | m.p. 67–68° C. |
| 9 | —$CH_2OCH_3$ | CP. | $Q_4$ | m.p. 135–136.5° C. |
| 10 | —$C_2H_5$ | —$CH_2OCH_3$ | $Q_4$ | |
| 11 | CP. | H | $Q_4$ | |
| 12 | —$CH_3$ | CP. | $Q_2$ | m.p. 91–93° C. |
| 13 | $SCH_3$ cyclopropyl | H | $Q_4$ | |
| 14 | —$CH_2OCH_3$ | H | $Q_1$ | |
| 15 | CP. | —$CH_3$ | $Q_1$ | |
| 16 | CP. | —$CH_2OCH_3$ | $Q_4$ | |
| 17 | —$CH_2OCH_3$ | —$CH_2OCH_3$ | $Q_4$ | |
| 18 | —$CH_3$ | CP. | $Q_3$ | m.p. 135–136° C. |
| 19 | —$C_2H_5$ | —$CH_2OC_2H_5$ | $Q_1$ | |
| 20 | cyclobutyl | —$CH_3$ | $Q_4$ | |

TABLE 1-continued

Compounds of formula $$\underset{R_1}{\overset{N}{\|}}\underset{S}{\overset{}{\diagdown}}\underset{}{\overset{R_2}{\diagup}}\underset{\overset{\|}{O}}{\overset{}{C}}-NH-\overset{CN}{\underset{}{C}}HR_3$$

| Comp. No. | $R_1$ | $R_2$ | $R_3$ | Physical constant |
|---|---|---|---|---|
| 21 | —CH$_2$OCH$_3$ | H | Q$_4$ | |
| 22 | —CH$_3$ | cyclobutyl | Q$_4$ | |
| 23 | —CH$_2$OC$_2$H$_5$ | CP. | Q$_4$ | |
| 24 | CP. | —CH$_3$ | Q$_4$ | m.p. 132–134° C. |
| 25 | —C$_2$H$_5$ | —CH$_2$OC$_2$H$_5$ | Q$_4$ | |
| 26 | CP. | —CH$_2$OCHF$_2$ | Q$_3$ | |
| 27 | —CH$_3$ | —CH$_2$OCH$_3$ | Q$_1$ | |
| 28 | —CH$_2$OCH$_3$ | —CH$_2$OCHF$_2$ | Q$_4$ | |
| 29 | cyclohexyl | —CH$_3$ | Q$_4$ | |
| 30 | —CH$_2$OC$_2$H$_5$ | —CH$_2$OCH$_3$ | Q$_1$ | |
| 31 | CP. | —CH$_3$ | Q$_2$ | |
| 32 | —CH$_3$ | —CH$_2$OCH$_3$ | Q$_3$ | m.p. 77–81° C. |
| 33 | CP. | —CH$_2$OC$_2$H$_5$ | Q$_1$ | |
| 34 | —C$_3$H$_7$-n | CP. | Q$_4$ | m.p. 114–115° C. |
| 35 | —CH$_2$OCH$_3$ | —CH$_3$ | Q$_1$ | m.p. 80–81° C. |
| 36 | —CH$_2$OC$_2$H$_5$ | H | Q$_4$ | |
| 37 | —CH$_2$OCH$_2$CH$_2$OCH$_3$ | —CH$_3$ | Q$_4$ | |
| 38 | —CH$_2$SCH$_3$ | —CH$_3$ | Q$_4$ | |
| 39 | CP. | —CH$_3$ | Q$_3$ | m.p. 127–130° C. |
| 40 | —CH$_3$ | —CH$_2$OCH$_3$ | Q$_2$ | |
| 41 | —CH$_2$OC$_2$H$_5$ | —CH$_2$OCH$_3$ | Q$_4$ | |
| 42 | CP. | —CH$_2$OC$_2$H$_5$ | Q$_4$ | |
| 43 | —CH$_2$OCHF$_2$ | H | Q$_4$ | |
| 44 | —C$_3$H$_7$-n | —CH$_2$OCH$_3$ | Q$_4$ | |
| 45 | 1-methylcyclopropyl | —CH$_2$OCH$_3$ | Q$_4$ | |
| 46 | 1-methylcyclopropyl | —CH$_3$ | Q$_4$ | |
| 47 | —CH$_2$OCH$_2$CH$_2$OCH$_3$ | CP. | Q$_4$ | |
| 48 | —CH$_2$OCH$_3$ | —CH$_3$ | Q$_2$ | m.p. 79–80° C. |
| 49 | —CH$_3$ | —CH$_2$OCH$_3$ | Q$_4$ | |
| 50 | —CH$_2$OCH$_2$CH=CH$_2$ | —CH$_3$ | Q$_4$ | |
| 51 | cyclopropyl-CH$_3$ | —CH$_2$OCH$_3$ | Q$_4$ | |
| 52 | —CH$_2$OCH$_2$CF$_3$ | H | Q$_4$ | |
| 53 | —CH$_3$ | —CH$_2$OC$_2$H$_5$ | Q$_1$ | |
| 54 | —CH$_2$OCH$_3$ | —CH$_3$ | Q$_3$ | m.p. 96–98° C. |
| 55 | —C$_3$H$_7$-iso | CP. | Q$_4$ | m.p. 132–133° C. |
| 56 | cyclopropyl-CH$_3$ | —CH$_3$ | Q$_4$ | |
| 57 | cyclopropyl-SCH$_3$ | CP. | Q$_4$ | |
| 58 | —CH$_2$OCH$_2$CH$_2$OCH$_3$ | —CH$_2$OCH$_3$ | Q$_4$ | |
| 59 | —CH$_3$ | —CH$_2$OC$_2$H$_5$ | Q$_4$ | |
| 60 | —CH$_2$O—CH$_2$—C≡CH | —CH$_3$ | Q$_4$ | |
| 61 | —CH$_2$O—C$_6$H$_5$ | —CH$_3$ | Q$_4$ | |
| 62 | —CH$_2$OCH$_2$CF$_3$ | —CH$_3$ | Q$_4$ | |
| 63 | —CH$_2$OCHF$_2$ | CP. | Q$_4$ | |

TABLE 1-continued

Compounds of formula

| Comp. No. | R₁ | R₂ | R₃ | Physical constant |
|---|---|---|---|---|
| 64 | $\overset{SCH_3}{\triangle}$ | —CH₂OCH₃ | Q₁ | |
| 65 | CP. | —C₂H₅ | Q₁ | |
| 66 | —CH₃ | —CH₂OC₃H₇-iso | Q₄ | |
| 67 | $\overset{SCH_3}{\triangle}$ | —CH₃ | Q₁ | |
| 68 | —CH₂OCH₃ | —CH₃ | Q₄ | m.p. 111–113° C. |
| 69 | —CH₂O—C₆H₄—F | —CH₃ | Q₄ | |
| 70 | —CH₂OC₂H₅ | —CH₃ | Q₁ | |
| 71 | $\overset{SCH_3}{\triangle}$ | —CH₂OCH₃ | Q₄ | |
| 72 | —CH₂OCHF₂ | —CH₂OCH₃ | Q₁ | |
| 73 | —CH₃ | —CH₂OCHF₂ | Q₁ | |
| 74 | $\overset{SCH_3}{\triangle}$ | —CH₃ | Q₃ | |
| 75 | —C₃H₇-iso | —CH₂OC₂H₅ | Q₄ | |
| 76 | —CH₂OCH₂—C₆H₅ | —CH₃ | Q₄ | |
| 77 | CP. | —C₂H₅ | Q₄ | m.p. 116–117.5° C. |
| 78 | —C₂H₅ | CP. | Q₂ | m.p. 84–86° C. |
| 79 | —CH₂OC₂H₅ | —CH₃ | Q₂ | |
| 80 | $\overset{SCH_3}{\triangle}$ | —CH₃ | Q₂ | |
| 81 | —C₄H₉-n | CP. | Q₁ | |
| 82 | $\overset{SCH_3}{\triangle}$ | —CH₂OC₂H₅ | Q₁ | |
| 83 | —CH₃ | —CH₂OCHF₂ | Q₄ | |
| 84 | —CH₂OCHF₂ | —CH₂OCH₃ | Q₄ | |

TABLE 1-continued

Compounds of formula $$\underset{R_1}{\overset{N}{\|}} \underset{S}{\overset{}{\diagdown}} \underset{}{\overset{R_2}{\diagdown}} C - NH - \underset{}{\overset{CN}{\underset{|}{C}}} HR_3$$
$$\phantom{aaaaaaaaaaaaaa} \| \phantom{aa}$$
$$\phantom{aaaaaaaaaaaaaaaa} O$$

| Comp. No. | R₁ | R₂ | R₃ | Physical constant |
|---|---|---|---|---|
| 85 | $-CH_2OCH_2$-(4-Cl-phenyl) | $-CH_3$ | $Q_4$ | |
| 86 | CP. | CP. | $Q_1$ | m.p. 86–88° C. |
| 87 | (1-SCH₃-cyclopropyl) | $-CH_3$ | $Q_4$ | |
| 88 | $-CH_3$ | $-CH_2OCH_2CF_3$ | $Q_4$ | |
| 89 | $-CH_2OCH_2CF_3$ | CP. | $Q_4$ | |
| 90 | $-C_2H_5$ | CP. | $Q_4$ | m.p. 81–83° C. |
| 91 | (1-SCH₃-cyclopropyl) | $-CH_2OC_2H_5$ | $Q_4$ | |
| 92 | $-C_4H_9$-n | CP. | $Q_4$ | |
| 93 | $-CH_2OC_2H_5$ | $-CH_3$ | $Q_3$ | $n_D^{25}$ 1.5723 |
| 94 | $-C_2H_5$ | CP. | $Q_1$ | m.p. 73–75° C. |
| 95 | $-CH_2OCH_3$ | CP. | $Q_1$ | m.p. 81–83° C. |
| 96 | $-CH_2OC_2H_5$ | $-CH_3$ | $Q_4$ | |
| 97 | $-C_2H_5$ | $-CH_2OCH_3$ | $Q_1$ | |
| 98 | $-CH_2OCHF_2$ | $-CH_3$ | $Q_1$ | |
| 99 | $-CH_2OCH_2CF_3$ | $-CH_2OCH_3$ | $Q_4$ | |
| 100 | (1-SCH₃-cyclopropyl) | $-C_2H_5$ | $Q_4$ | |
| 101 | $-CH_2OCHF_2$ | $-C_2H_5$ | $Q_4$ | |
| 102 | $-CH_2OCH(CH_3)-C_2H_5$ | $-CH_3$ | $Q_4$ | |
| 103 | $-CH_2OCH_2CH_2OCH_3$ | $-CH_3$ | $Q_1$ | |
| 104 | $-CH_2OCH_3$ | $-C_2H_5$ | $Q_4$ | m.p. 111–112° C. |
| 105 | $-CH_2OCHF_2$ | $-CH_3$ | $Q_4$ | |
| 106 | $-CH_2OCH_2CF_3$ | $-C_2H_5$ | $Q_4$ | |
| 107 | CP. | $-C_3H_7$-iso | $Q_4$ | m.p. 108–111° C. |
| 108 | $-CH_2OCHF_2$ | $-C_3H_7$-iso | $Q_1$ | |
| 109 | $-CH_2OC_2H_5$ | $-C_2H_5$ | $Q_1$ | |
| 110 | $-CH_2OCHF_2$ | $-CH_3$ | $Q_2$ | oil |
| 111 | $-CH_2OC_2H_5$ | $-C_2H_5$ | $Q_4$ | m.p. 126–129° C. |
| 112 | (1-SCH₃-cyclopropyl) | $-C_3H_7$-n | $Q_4$ | |
| 113 | $-CH_2OCH_3$ | $-C_3H_7$-iso | $Q_4$ | |
| 114 | $-CH_2OCHF_2$ | $-C_3H_7$-iso | $Q_4$ | |
| 115 | $-CH_2OCH_2CH_2OCH_3$ | $-C_2H_5$ | $Q_4$ | |
| 116 | $-CH_2OC_2H_5$ | $-C_3H_7$-iso | $Q_4$ | |
| 117 | $-CH_2OCH_2CF_3$ | $-CH_3$ | $Q_1$ | |
| 118 | $-CH_2OC_2H_5$ | $-C_2H_5$ | $Q_3$ | m.p. 96–97° C. |
| 119 | $-CH_2OCH_3$ | $-C_2H_5$ | $Q_3$ | m.p. 78–83° C. |
| 120 | CP. | $-C_2H_5$ | $Q_3$ | m.p. 106–109° C. |
| 121 | $-CH_2OCH_3$ | CP. | $Q_3$ | m.p. 104–106° C. |
| 122 | $-CH_2OCH_3$ | $-C_2H_5$ | $Q_2$ | m.p. 81–83° C. |

TABLE 1-continued

Compounds of formula

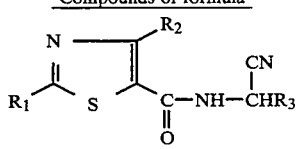

| Comp. No. | $R_1$ | $R_2$ | $R_3$ | Physical constant |
|---|---|---|---|---|
| 123 | —$CH_2OCH_3$ | CP. | $Q_2$ | m.p. 105–106° C. |
| 124 | —$CH_2OCH_3$ | —$C_2H_5$ | $Q_1$ | m.p. 104–105° C. |
| 125 | —$C_3H_7$iso | CP. | $Q_1$ | m.p. 89–92° C. |
| 126 | —$C_3H_7$iso | CP. | $Q_3$ | m.p. 129–131° C. |
| 127 | —$C_3H_7$iso | CP. | $Q_2$ | m.p. 109–110° C. |
| 128 | —$C_3H_7$n | CP. | $Q_1$ | m.p. 86–87° C. |
| 129 | —$C_3H_7$n | CP. | $Q_3$ | m.p. 74–76° C. |
| 130 | —$C_3H_7$n | CP. | $Q_2$ | m.p. 81–83° C. |
| 131 | —$CH_2OCHF_2$ | $CH_3$ | $Q_3$ | |
| 132 | —$CH_2OCHF_2$ | $C_2H_5$ | $Q_1$ | |
| 133 | —$CH_2OCHF_2$ | $C_2H_5$ | $Q_2$ | |
| 134 | —$CH_2OCHF_2$ | $C_2H_5$ | $Q_3$ | |
| 135 | —$CH_2OCHF_2$ | CP. | $Q_1$ | |
| 136 | —$CH_2OCHF_2$ | CP. | $Q_2$ | |
| 137 | —$CH_2OCHF_2$ | CP. | $Q_3$ | |
| 138 | CP. | CP. | $Q_2$ | m.p. 103–105° C. |
| 139 | CP. | CP. | $Q_3$ | m.p. 123–126° C. |
| 140 | CP. | —$C_3H_7$-n | $Q_1$ | m.p. 106–108° C. |
| 141 | CP. | —$C_3H_7$iso | $Q_2$ | m.p. 108–110° C. |
| 142 | CP. | —$C_3H_7$iso | $Q_1$ | m.p. 97–100° C. |
| 143 | —$CH_2OCH_3$ | —$C_3H_7$iso | $Q_3$ | m.p. 89–91° C. |
| 144 | CP. | —$C_3H_7$-n | $Q_2$ | m.p. 111–114° C. |
| 145 | CP. | —$C_3H_7$iso | $Q_3$ | m.p. 101–103° C. |
| 146 | —$CH_2OC_2H_5$ | CP. | $Q_1$ | m.p. 116–118° C. |
| 147 | —$CH_2OCH_3$ | —$C_3H_7$-n | $Q_3$ | m.p. 98–101° C. |
| 148 | —$CH_2OC_2H_5$ | CP. | $Q_3$ | m.p. 123–125° C. |
| 149 | —$CH_2OCH_3$ | —$C_3H_7$iso | $Q_1$ | m.p. 87–90° C. |
| 150 | —$CH_2OCH_3$ | —$C_3H_7$-n | $Q_1$ | m.p. 91–94° C. |
| 151 | CP. | —$C_3H_7$-n | $Q_3$ | m.p. 103–106° C. |
| 152 | —$CH_2OCH_3$ | —$C_3H_7$-n | $Q_2$ | m.p. 85–87° C. |
| 153 | —$CH_2OCH_3$ | —$C_3H_7$iso | $Q_2$ | m.p. 93–95° C. |
| 154 | CP. | —$C_3H_7$-n | $Q_4$ | m.p. 114–120° C. |
| 155 | —$CH_2OCH_3$ | —$C_3H_7$-n | $Q_4$ | m.p. 124–126° C. |
| 156 | —$CH_2OC_2H_5$ | CP. | $Q_2$ | m.p. 109–111° C. |

$Q_1$ = 2-furanyl
$Q_2$ = 3-furanyl
$Q_3$ = 2-thienyl
$Q_4$ = 3-thienyl
CP. = cyclopropyl

TABLE 2

Intermediates of formula V

| Comp. No. | $R_1$ | $R_2$ | Physical constant |
|---|---|---|---|
| 2.1 | CP. | $CH_3$ | m.p. 198–200° C. |
| 2.2 | CP. | $C_2H_5$ | m.p. 96–97° C. |
| 2.3 | CP. | $C_3H_7$-n | m.p. 104–106° C. |
| 2.4 | CP. | $C_3H_7$-iso | m.p. 84–87° C. |
| 2.5 | $CH_3$ | CP. | m.p. 190–191° C. |
| 2.6 | $C_2H_5$ | CP. | m.p. 158–159° C. |
| 2.7 | $C_3H_7$-iso | CP. | m.p. 122–123° C. |
| 2.8 | $C_3H_7$-n | CP. | m.p. 161–162° C. |
| 2.9 | —$CH_2OCH_3$ | $CH_3$ | m.p. 168–169.5° C. |
| 2.10 | —$CH_2OCH_3$ | $C_2H_5$ | m.p. 146–147° C. |
| 2.11 | —$CH_2OCH_3$ | CP. | m.p. 159–161° C. |
| 2.12 | —$CH_2OC_2H_5$ | $CH_3$ | m.p. 185–186° C. |
| 2.13 | —$CH_2OC_2H_5$ | $C_2H_5$ | m.p. 114–115° C. |
| 2.14 | —$CH_2OC_2H_5$ | CP. | m.p. 132–134° C. |
| 2.15 | CP. | CP. | m.p. 102–104° C. |
| 2.16 | —$CH_2OCHF_2$ | $CH_3$ | |
| 2.17 | —$CH_2OCHF_2$ | $C_2H_5$ | |
| 2.18 | —$CH_2OCHF_2$ | CP. | |
| 2.19 | —$CH_2OCH_3$ | $C_3H_7$-n | m.p. 137–139° C. |
| 2.20 | —$CH_2OCH_3$ | $C_3H_7$-iso | m.p. 148–151° C. |

CP. = cyclopropyl

In the presence of an acid catalyst, such as HCl, it is readily possible to obtain the corresponding carboxylic acid $C_1$–$C_6$alkyl esters from the acids of Table 2 by esterification with methanol, ethanol or one of the isomeric alcohols propanol, pentanol and hexanol.

2. Formulation Examples for active ingredients of formula I (throughout percentages are by weight)

| 2.1. Wettable powder | a) | b) | c) |
|---|---|---|---|
| a compound of Table 1 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |

-continued

| 2.1. Wettable powder | a) | b) | c) |
|---|---|---|---|
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.2. Emulsifiable concentrate | |
|---|---|
| a compound of Table 1 | 10% |
| octylphenol polyethylene glycol ether (4-5 moles of ethylene oxide) | 3% |
| calcium dodecylbenzenesulfonate | 3% |
| cyclohexanone | 34% |
| xylene mixture | 50% |

Emulsions of any required concentration can be produced from this concentrate by dilution with water.

| 2.3. Dusts | a) | b) |
|---|---|---|
| a compound of Table 1 | 5% | 8% |
| talcum | 95% | — |
| kaolin | — | 92% |

Ready-for-use dusts are obtained by mixing the active ingredient with the carrier, and grinding the mixture in a suitable mill.

| 2.4. Extruder granulate | |
|---|---|
| a compound of Table 1 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and subsequently dried in a stream of air.

| 2.5. Coated granulate | |
|---|---|
| a compound of Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.6. Suspension concentrate | |
|---|---|
| a compound of Table 1 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. Biological Examples

I. Action against Phytophthora infestans on tomato plants a) Curative Action

After a cultivation period of 3 weeks, tomato plants of the "Roter Gnom" variety are sprayed with a zoospore suspension of the fungus and incubated in a cabinet at 18° to 20° and saturated humidity. The humidification is discontinued after 24 hours. When the plants have dried, they are sprayed with a mixture containing a wettable powder formulation of the test compound in a concentration of 600, 200 or 60 ppm. When the spray-coating has dried, the plants are returned to the humidity cabinet for four days. The effectiveness of the test compounds is evaluated on the basis of the number and size of the typical leaf specks occurring after that time.

b) Preventive Systemic Action

A wettable powder formulation of the test compound is applied in a concentration of 60 ppm (based on the volume of the soil) to the surface of the soil of three-week-old tomato plants of the "Roter Gnom" variety in pots. After three days the underside of the leaves of the plants are sprayed with a zoospore suspension of Phytophthora infestans. The plants are then kept in a spraying cabinet at 18° to 20° C. and saturated humidity for 5 days. The effectiveness of the test compounds is evaluated on the basis of the number and size of the typical leaf specks that form after that time.

The following compounds of Table 1 inhibit disease attack to less than 10%: Nos. 2, 3, 5, 8, 9, 12, 18, 24, 32, 34, 35, 39, 48, 54, 55, 63, 68, 77, 78, 90, 93, 95, 98, 104, 107, 110, 111, 113, 116, 118 to 130 and 138 to 156.

II. Action against Plasmopara viticola (Bert.et Curt.) (Berl et DeToni) on vines a) Residual Preventive Action Vine cuttings of the "Chasselas" variety are raised in a greenhouse. In the 10-leaf stage, 3 plants are sprayed with a mixture prepared from a wettable powder formulation of the test compound (200 ppm of active ingredient). After the spray-coating has dried, the undersides of the leaves of the plants are uniformly infected with a spore suspension of the fungus. The plants are then kept in a humidity chamber for 8 days. After this time the control plants exhibit clear symptoms of disease. The effectiveness of the test compounds is evaluated on the basis of the number and size of the infection sites on the treated plants.

b) Curative action

Vine cuttings of the "Chasselas" variety are raised in a greenhouse and in the 10-leaf stage the undersides of the leaves are infected with a spore suspension of Plasmopara viticola. After 24 hours in a humidity chamber the plants are sprayed with an active ingredient mixture prepared from a wettable powder formulation of the test compound (500 ppm of active ingredient). The plants are then kept in the humidity cabinet for a further 7 days. After this time the control plants exhibit clear symptoms of disease. The effectiveness of the test compounds is evaluated on the basis of the number and size of the infection sites on the treated plants.

In this test too, all the compounds mentioned in Example 1 inhibit disease attack to less than 10%.

III. Action against Pythium debaryanum on sugar beet (Beta vulgaris)

a) Action after Soil Application

The fungus is cultured on sterile oat grains and added to a soil/sand mixture. The infected soil is introduced into pots and sown with sugar beet seeds. Immediately after sowing, wettable powder formulations of the test compounds in the form of aqueous suspensions are poured onto the soil (20 ppm of active ingredient, based on the volume of the soil). The pots are then placed in a greenhouse at 20°-b 24° C. for 2-3 weeks. The soil is kept constantly uniformly wet by lightly spraying with water. The test is evaluated by determining the emergence rate of the sugar beet plants and the proportion of healthy and diseased plants.

b) Action after Dressing

The fungus is cultured on sterile oat grains and added to a soil/sand mixture. The infected soil is introduced into pots and sown with sugar beet seeds that have been dressed with a dressing powder formulation of the test compounds (1000 ppm of active ingredient, based on the weight of the seeds). The pots are placed in a greenhouse at 20°-24° C. for 2-3 weeks. The soil is kept uniformly wet by lightly spraying with water. The test is evaluated by determining the emergence rate of the sugar beet plants and the proportion of healthy and diseased plants.

An emergence rate of more than 80% is obtained with compounds of Table 1. The corresponding control plants exhibit an emergence rate of less than 30% and have an unhealthy appearance.

I claim:

1. Thiazolyl-5-carbonamide derivatives of formula I and acid addition salts and metal salt complexes thereof

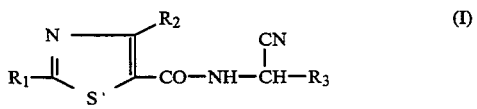

wherein $R_3$ is 2-furanyl, 2-thienyl, 3-furanyl or 3-thienyl; and wherein $R_1$ and $R_2$ each independently of the other have the following meanings:

a) $C_3$-$C_6$cycloalkyl that is unsubstituted or substituted by methyl or methylthio, b) the group —$CH_2$—X—$R_4$, and c) one of the two substituents $R_1$ and $R_2$ may also be hydrogen or $C_1$-$C_4$alkyl, wherein X is oxygen or sulfur, and $R_4$ is $C_1$-$C_4$alkyl that may be unsubstituted or substituted by halogen or, in the case of $C_2$-$C_4$alkyl, also by $C_1$-$C_3$alkoxy, or wherein $R_4$ is $C_3$-$C_4$alkenyl, $C_3$-$C_4$alkynyl or a phenyl group or benzyl group of which the aromatic ring is unsubstituted or may be substituted by halogen, $C_1$-$C_2$alkyl, $C_1$-$C_2$alkoxy, $CF_3$ or by $NO_2$.

2. Compounds of formula I according to claim 1, wherein one of the two substituents $R_1$ and $R_2$ is $C_3$-$C_6$cycloalkyl that is unsubstituted or substituted by methyl or methylthio, and the other substituent is d) cyclobutyl, cyclopropyl, methylcyclopropyl or methylthiocyclopropyl, e) the group —$CH_2$—X—$R_4$ or f) hydrogen or $C_1$-$C_4$alkyl, while $R_3$, X and $R_4$ are as defined above.

3. Compounds of formula I according to claim 2, wherein one of the two substituents $R_1$ and $R_2$ is $C_3$-$C_6$cycloalkyl and the other is cyclobutyl or cyclopropyl, while $R_3$ is as defined above.

4. Compounds of formula I according to claim 3, wherein $R_1$ and $R_2$ are cyclopropyl.

5. Compounds of formula I according to claim 2, wherein $R_1$ is hydrogen, $C_1$-$C_4$alkyl or the group —$CH_2$—X—$R_4$, X is oxygen or sulfur, and $R_4$ is $C_1$-$C_4$alkyl that is unsubstituted or substituted by fluorine or, in the case of $C_2$-$C_4$alkyl, may also be substituted by $C_1$-$C_3$alkoxy; or wherein $R_4$ is allyl, propargyl, phenyl or benzyl, the aromatic rings of the latter radicals being unsubstituted or substituted by one or two of the substituents fluorine, chlorine, methyl, ethyl, methoxy and $CF_3$, while $R_2$ is $C_3$-$C_6$cycloalkyl that is unsubstituted or substituted by methyl or methylthio, while $R_3$ is as defined above.

6. Compounds according to claim 5, wherein $R_1$ is hydrogen, $C_1$-$C_4$alkyl or —$CH_2$—O—$R_4$, $R_2$ is cyclobutyl, cyclopropyl, methylcyclopropyl or methylthiocyclopropyl, and $R_4$ is $C_1$-$C_4$alkyl that is unsubstituted or fluoro-substituted or, in the case of $C_2$-$C_4$alkyl, may also be substituted by methoxy or ethoxy; or wherein $R_4$ is allyl, propargyl, phenyl, chlorophenyl, fluorophenyl, benzyl, chlorobenzyl or fluorobenzyl, while $R_3$ is as defined above.

7. Compounds according to claim 6, wherein $R_2$ is cyclopropyl, and $R_4$ is methyl, ethyl, fluoromethyl, difluoromethyl, trifluoroethyl, allyl, propargyl, phenyl or benzyl.

8. Compounds according to claim 7, wherein $R_1$ is hydrogen, $C_1$-$C_3$alkyl, methoxymethyl or ethoxymethyl.

9. Compounds of formula I according to claim 1, wherein either a) $R_1$ is $CH_3$, $C_2H_5$, n-propyl, isoC$_3$H$_7$, $CH_2$—O—$CH_3$, $CH_2$—O—$C_2H_5$, $CH_2$—O—$CHF_2$ or cyclopropyl, and $R_2$ is cyclopropyl, or wherein b) $R_1$ is $CH_2$—O—$CH_3$, $CH_2$—O—$C_2H_5$, $CH_2$—O—$CHF_2$ or cyclopropyl and $R_2$ is CFC$_3$-alkyl, and $R_3$ is as defined above.

10. Compounds of formula I according to claim 9, wherein $R_1$ is methyl, ethyl, n-propyl or isopropyl and $R_2$ is cyclopropyl.

11. Compounds of formula I according to claim 9, wherein $R_1$ is $CH_2$—O—$CH_3$, $CH_2$—O—$C_2H_5$ or cyclopropyl and $R_2$ is methyl, ethyl, n-propyl, isopropyl or cyclopropyl.

12. A microbicidal composition for the control of plant diseases containing as active ingredient a compound of formula I together with a suitable carrier therefor.

13. A method of controlling plant diseases or preventing attack by disease, which comprises the application of a compound of formula I to the plants, to their growing site, to parts of the plants or to plant propagation material.

* * * * *